United States Patent [19]
Fischer et al.

[11] Patent Number: 5,461,175
[45] Date of Patent: Oct. 24, 1995

[54] METHOD FOR SEPARATING ENANTIOMERS OF ARYLOXIPROPANOLAMINE DERIVATIVES, AND CHIRAL SOLID-PHASE CHROMATOGRAPHY MATERIAL FOR USE IN THE METHOD

[76] Inventors: Lutz Fischer, Ludwigstrasse 18, D-3300 Braunschweig; Ralf Müller, Gorch-Fock Strasse 25, D-2359 Henstedt-Ulzburg, both of Germany; Klaus Mosbach, Lackalänga 31, Pl 5548, S-244 94 Furulund; Björn Ekberg, Vinstrupsgatan 12, S-222 22 Lund, both of Sweden

[21] Appl. No.: 232,110

[22] PCT Filed: Oct. 30, 1992

[86] PCT No.: PCT/SE92/00751

§ 371 Date: Jul. 8, 1994

§ 102(e) Date: Jul. 8, 1994

[87] PCT Pub. No.: WO93/09075

PCT Pub. Date: May 13, 1993

[30] Foreign Application Priority Data

Nov. 4, 1991 [SE] Sweden .................................. 9103234

[51] Int. Cl.$^6$ ........................... C07B 57/00; B01D 15/08
[52] U.S. Cl. ...................... 564/304; 210/656; 524/719; 524/724; 544/134; 564/348; 564/349
[58] Field of Search .................................. 564/304, 348, 564/349; 544/134; 210/656; 524/719, 724

OTHER PUBLICATIONS

J. Am. Chem. Soc., vol. 13, 1991, "Direct Enantioseparation of β–Adrenergic Blockers Using a Chiral Stationary Phase Prepared by Molcular Imprinting", Lutz Fischer et al.

Journal of Chromatography, vol. 516, (1990) pp. 313–322, "Enantiomeric Resolution on Molecularly Imprinted Polymers Prepared With Only Non–Covalent and Non–Ionic Interactions", Lars I. Andersson et al.

Journal of Chromatography, vol. 516, (1990), pp. 323–331, "Enantiomeric Resolution of Amino Acid Derivatives on Molecularly Imprinted Polymers as Monitored by Potentiometric Measurements", Lars I. Andersson et al.

Journal of Chromatography, vol. 470, (1989), pp. 391–399, "Recent Advances in the Preparation and Use of Molecularly Imprinted Polymers for Enantiometric Resolution of Amino Acid Derivatives", Daniel J. O'Shannessy et al.

J. Am. Chem. Soc., vol. 110, (1988), pp. 5853–5860, "Highly Enantioselective and Substrate–Selective Polymers Obtained by Molecular Imprinting Utilizing Noncovalent Interactions. NMR and Chromatographic Studies on the Nature of Recognition", Börje Sellergren et al.

Journal of Liquid Chromatography, vol. 13, No. 15, (1990), pp. 2987–3000, "Template Imprinted Polymers for HPLC Separation of Racemates", Günter Wulff et al.

Journal of Molecular Recognition, vol. 2, No. 1, (1989) pp. 1–5, "Molecular Recognition in Synthetic Polymers", Daniel J. O'Shannessy et al.

Tibtech, Apr. 1989, vol. 7, "Molecular Imprinting: A Technique for Producing Specific Separation Materials", Björnm Ekberg et al.

*Primary Examiner*—Peter O'Sullivan
*Attorney, Agent, or Firm*—Burns, Doane, Swecker & Mathis

[57] ABSTRACT

A method for separating enantiomers of a derivative of an aryloxipropanolamine is disclosed, characterized in that the derivative is contacted with a chiral solid-phase chromatography material containing molecular imprints of an optically pure enantiomer of the derivative to be separated.

14 Claims, 2 Drawing Sheets

(S)-(-)-TIMOLOL
USED AS PRINT MOLECULE

ATENOLOL

METOPROLOL

PROPRANOLOL

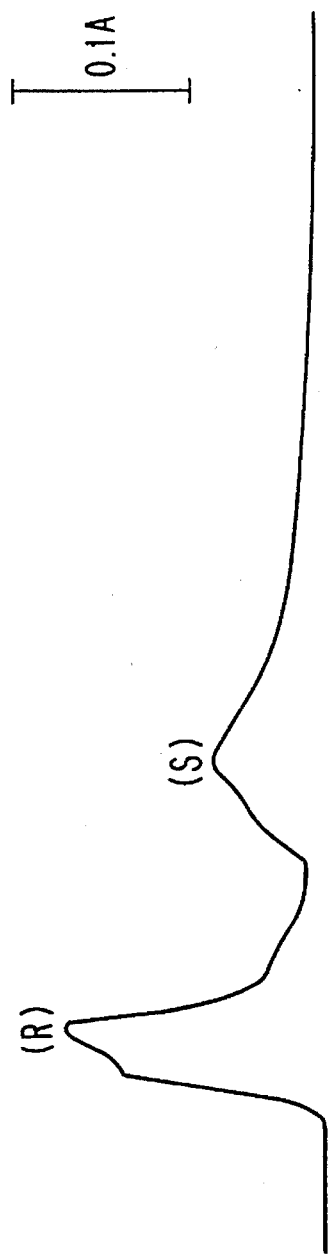
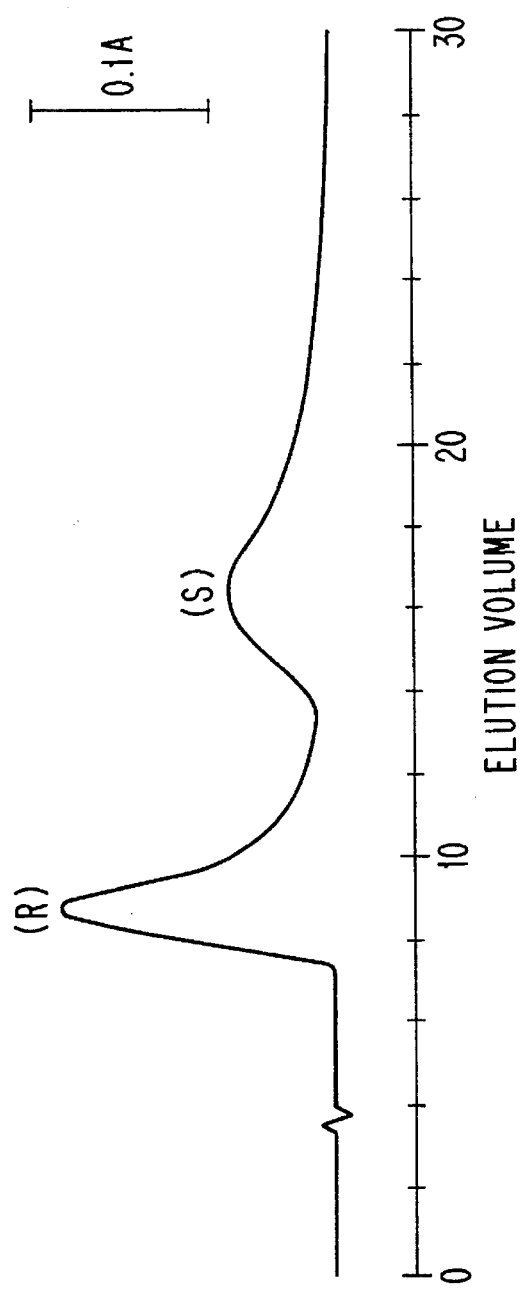
FIG. 2(A)
FIG. 2(B)

METHOD FOR SEPARATING ENANTIOMERS OF ARYLOXIPROPANOLAMINE DERIVATIVES, AND CHIRAL SOLID-PHASE CHROMATOGRAPHY MATERIAL FOR USE IN THE METHOD

This application is a 371 of PCT/SE92/00751 filed 30 Oct. 1995.

The present invention relates to a method for separating enantiomers of derivatives of aryloxipropanolamines and a chiral solid-phase chromatography material for use in the method. The invention also relates to the use of the molecular imprinting method for preparing the chiral solid-phase chromatography material.

β-adrenergic blocking compounds (or β-blockers) are important pharmaceutical preparations which are used in the treatment of hypertension, arrhythmia and angina pectoris. There is a great need of using optically pure enantiomers since the stereoisomers express a varying pharmacological activity, and in some cases they can also be used against various symptoms (1). Consequently, intensive research is in progress for preparing optically pure β-blockers, e.g. by using an asymmetric synthesis (2) including biocatalysts (3), a fractional crystallisation (4), as well as indirect (5) or direct (6) chromatographic separation of the enantiomorphs.

According to the present invention, a method is provided for separating enantiomers of derivatives of aryloxipropanolamines by means of a chiral solid-phase chromatograpy material (Chiral Stationary Phase=CSP), which is prepared by the so-called molecular imprinting method (7). The molecular imprinting method used is based on non-covalent complementary interactions between the non-derivatised print molecule and polymerisable monomers.

More precisely, a method is provided for separating enantiomers of derivatives of aryloxipropanolamines, in which the derivatives are contacted with a chiral solid-phase chromatography material containing molecular imprints of an optically pure enantiomer of the derivatives to be separated.

Moreover, a chiral solid-phase chromatography material is provided to be used in the separation of enantiomers of derivatives of aryloxipropanolamines, which material consists of a polymer prepared by polymerisation of a monomer in the presence of a cross-linking agent and of an optically pure enantiomer of the derivatives to be separated, a molecular imprint of the optically pure enantiomer being formed in the polymer by non-covalent interactions between the monomer and the optically pure enantiomer.

According to the invention, there is also provided the use of the molecular imprinting method for preparing a chiral solid-phase chromatography material to be used in the separation of enantiomers of derivatives of aryloxipropanolamines.

Suitable monomers for preparing the chiral solid-phase chromatography material are monomers with functional groups, such as carboxyl-functional monomers. Preferred monomers are methacrylic acid [MAA, $H_2C=C(CH_3)—COOH$] or itaconic acid [ITA, $H_2C=C(COOH)—(CH_2)—COOH$]. These two monomers can, by their functional groups, form non-covalent bonds in organic solvents to the print molecule. Itaconic acid has previously been used in polymer chemistry (8), but it has now surprisingly been found that this acid is highly suited for use as monomer in the preparation of molecular imprints.

The monomers are polymerised in the presence of a cross-linking agent, which results in a three-dimensional network being formed. One cross-linking agent is ethylene glycol dimethacrylate.

Furthermore, the monomers are polymerised in the presence of a so-called print molecule, i.e. in this case an optically pure enantiomer of the derivative to be separated. During the polymerisation, non-covalent complementary interactions arise between the non-derivatised print molecule and the polymerisable monomers. After the polymerisation, the print molecule is removed from the three-dimensional network by extraction with a suitable solvent. As a result, individual sites with complementary points of bonding will probably remain within the polymer.

As aryloxipropanolamine derivatives that can be separated by the method according to the invention, mention can be made of timolol, propranolol, metoprolol and atenolol (formulae, see FIG. 1).

The resolution of racemic mixtures of important non-derivatised pharmaceutical preparations, such as β-blockers, by using the molecular imprinting method brings great advantages, such as extremely pure preparations and a simple method without any complicated purification steps. With the materials tested according to the Examples, the separation properties were maintained for as long a period as 8 months and with more than 50 injections.

Contrary to previous methods, the method according to the invention offers a high degree of freedom, since it allows the preparation of specific materials with predictable selectivities as desired. By using the described method, it should be possible also on a technical scale to remove contaminating small amounts of an undesired enantiomer.

The invention will now be described in more detail by means of the following Examples and the accompanying Figures.

The expressions and abbreviations used in the Examples have the following meanings:

$R_S$=resolution
$k'_R=(t_R-t_O)/t_O$
$k'_S=(t_S-T_O)/t_O$
$\alpha=K'_S/k'_R$
$k'_R$=the capacity factor for the (R)-(+)-enantiomer
$k'_S$=the capacity factor for the (S)-(−)-enantiomer
$k'_{rac}$=the capacity factor for the racemate
$t_O$=the retention period for non-retained, dissolved substances, the retention period being determined by injecting acetone
$R_S$ determined graphically (7)

FIG. 2 shows a diagram of chromatographic resolution of timolol on polymers containing (A) methacrylic acid and (B) itaconic acid.

EXAMPLE 1

Figure 1:
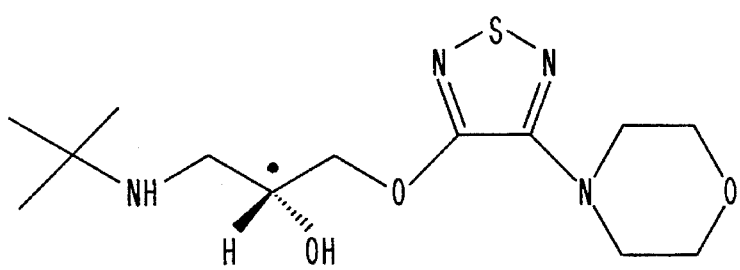
FIG. 1 illustrates structures of various tested β-blockers. The (S)-(−)-configuration of timolol was used as print molecule for the preparation of the chiral stationary phase (CSP).
Figure 1:
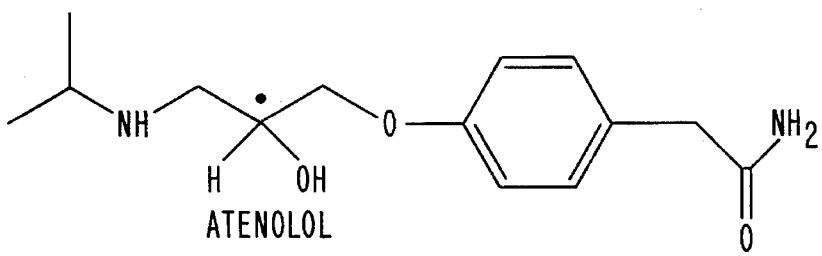
Figure 1:
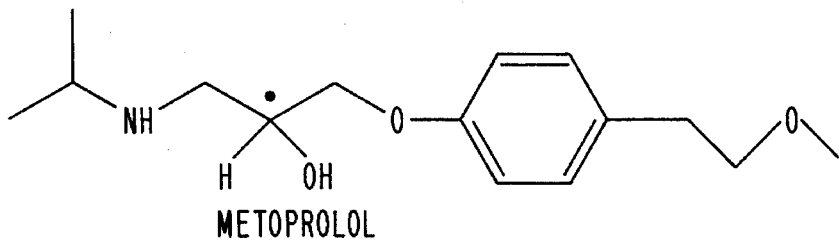
Figure 1:
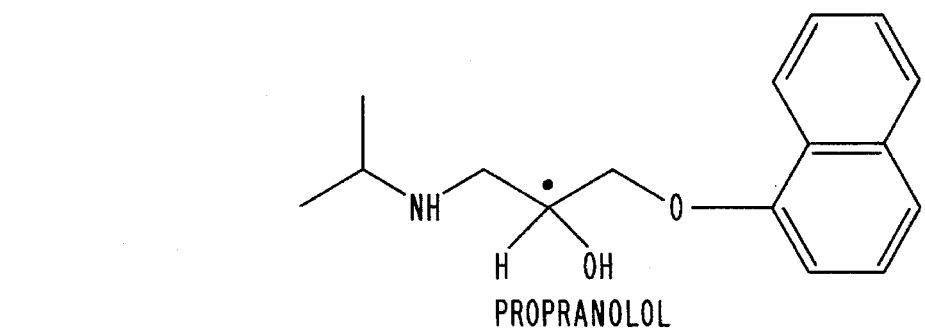

Preparation of a polymer selective for (S)(−)-timolol 632.8 g (2 mmol) (S)(−)-timolol is resolved in a 50 ml test tube in a mixture of 16 ml tetrahydrofuran, 1561.2 mg (12 mmol) itaconic acid, 12.48 ml (60 mmol) ethylene glycol dimethacrylate and 180 mg (1.1 mmol) 2.2'-azobis(2-methylpropionitrile). The solution is cooled in an ice bath, and nitrogen gas is caused to flow through the solution for 20 min. The test tube is sealed. The tube is placed in a freezing chamber (−20° C.) and exposed to UV-light at the wave length of 366 nm for 24 h.

The polymer formed is manually ground up in a mortar and then dried in a vacuum-type desiccator for 3 h. The polymer is further ground in a mechanical mortar device (Retsch, Haan, Germany) for 20 min. The material is screened through a 25 μm screen. The remaining material is ground and screened in two more turns. Small polymer particles from the screened material are removed by a sedimentation process in acetonitrile for 30 min in five turns.

The resulting material is packed in an HPLC steel column (200×4.6 mm) in chloroform/acetonitrile (v/v, 3/17) at a pressure of 300 bars.

The column is arranged in an HPLC device (LKB, Bromma, Sweden) and washed therein with acetic acid/acetonitrile (v/v, 1/4) at a flow rate of 1 ml/min, for 1 h. Subsequently, the column is equilibrated in ethanol/tetrahydrofuran/acetic acid (v/v/v, 50/40/10) at a flow rate of 1 ml/min, a pressure of 30 bars and detection at 294 nm.

20 μg (R,S)-timolol is injected in 20 μl of the eluant ethanol/tetrahydrofuran/acetic acid (v/v/v, 50/40/10). $k'_R=1.4$ $k'_S=3.5$ $\alpha=2.5$ $R_S=1.9$

EXAMPLE 2

Preparation of a polymer selective for (S)(−)-propranolol:

389.01 mg (1.5 mmol) (S)(−)-propranolol is resolved in a 50 ml test tube in a mixture of 6 ml chloroform, 537 mg (6 mmol) methacrylate, 4.985 ml (24 mmol) ethylene glycol dimethacrylate and 56 mg (0.34 mmol) 2.2'-azobis(2-methylpropionitrile). The solution is cooled in an ice bath, and nitrogen gas is caused to flow through the solution for 20 min. The test tube is sealed. The tube is placed in a cooling chamber (+4° C.) and exposed to UV-light at the wave length of 366 nm for 24 h.

The polymer formed is ground up manually in a mortar and then dried in a vacuum-type desiccator for 3 h. The polymer is further ground in a mechanical mortar device (Retsch, Haan, Germany) for 20 min. The material is screened through a 25 μm screen. The remaining material is ground and screened in two more turns. Small polymer particles from the screened material are removed by a sedimentation process in acetonitrile for 30 min in five turns.

The resulting material is packed in an HPLC steel column (200×4.6 mm) in chloroform/acetonitrile (v/v, 3/17) at a pressure of 300 bars.

The column is arranged in an HPLC device (LKB, Bromma, Sweden) and washed therein with acetic acid/acetonitrile (v/v, 1/9) at a flow rate of 1 ml/min for 1 h. Subsequently, the column is equilibrated in acetonitrile/acetic acid (v/v, 93/7) at a flow rate of 1 ml/min, a pressure of 30 bars and detection at 275 nm. 20 μg (R,S)-propranolol is injected in 20 μl of the eluant acetonitrile/acetic acid (v/v, 93/7). $k'_R=1.0$ $k'_S=2.8$ $\alpha=2.8$ $R_S=1.4$

EXAMPLE 3

Preparation of a polymer selective for (S)(−)-atenolol:

399.5 mg (1.5 mmol) (S)(−)-atenolol is resolved in a 50 ml test tube in a mixture of 6 ml chloroform, 537 mg (6 mmol) methacrylate, 4.985 ml (24 mmol) ethylene glycol dimethacrylate and 56 mg (0.34 mmol) 2.2'-azobis(2-methyl propionitrile). The solution is cooled in an ice bath, and nitrogen gas is caused to flow through the solution for 20 min. The test tube is sealed. The tube is placed in a cooling chamber (+4° C.) and exposed to UV-light at the wave length of 366 nm for 24 h.

The polymer formed is ground up manually in a mortar and then dried in a vacuum-type desiccator for 3 h. The polymer is further ground in a mechanical mortar device (Retsch, Haan, Germany) for 20 min. The material is screened through a 25 μm screen. The remaining material is ground and screened in two more turns. Small polymer particles from the screened material are removed by a sedimentation process in acetonitrile for 30 min in five turns.

The resulting material is packed in an HPLC steel column (200+4.6 mm) in chloroform/acetonitrile (v/v, 3/17) at a pressure of 300 bars.

The column is arranged in an HPLC device (LKB, Bromma, Sweden) and washed therein with acetic acid/acetonitrile (v/v 1/9) at a flow rate of 1 ml/min for 1 h. Subsequently, the column is equilibrated in acetonitrile/acetic acid (v/v, 93/7) at a flow rate of 1 ml/min, a pressure of 30 bars and detection at 275 nm.

20 μg (R,S)-atenolol is injected in 20 μl of the eluant acetonitrile/acetic acid (v/v, 93/7). $k'_R=1.18$ $k'_S=2.34$ $\alpha=2.0$ $R_S=0.5$

EXAMPLE 4

Preparation of a polymer selective for (S)(−)metoprolol 535 mg (2 mmol) (S)(−)-metoprolol is resolved in a 50 ml test tube in a mixture of 6 ml chloroform, 537 mg (6 mmol) methacrylate, 4.985 ml (24 mmol) ethylene glycol dimethacrylate and 56 mg (0.34 mmol) 2.2'-azobis(2-methyl propionitrile). The solution is cooled in an ce bath, and nitrogen gas is caused to flow through the solution for 20 min. The test tube is sealed. The tube is placed in a cooling chamger (+4° C.) and exposed to UV-light at the wave length of 366 nm for 24 h.

The polymer formed is ground up manually in a mortar and then dried in a vaccum-type desiccator for 3 h. The polymer is further ground in a mechanical mortar device (Retsch, Haan, Germany) for 20 min. The material is screened through a 25 μm screen. The remaining material is ground and screened in two more turns. Small polymer particles from the screened material are removed in a sedimentation process in acetonitrile for 30 min in five turns.

The resulting material is packed in an HPLC steel column (200×4.6 mm) in chloroform/acetonitrile (v/v, 3/17) at a pressure of 300 bars.

The column is arranged in an HPLC divice (LKB, Bromma, Sweden) and washed therein with acetic acid/acetonitrile (v/v, 1/9) at a flow rate of 1 nl/min for 1 h. Subsequently, the column is equilibrated in acetonitrile/acetic acid (v/v, 93/7) at a flow rate of 1 ml/min, a pressure of 30 bars and detection at 275 nm. 20 μg (R,S)-metprolol is injected in 20 μl of the eluant acetonitrile/acetic acid (v/v, 93/7). $k'_R=1.1$ $K'_S=3.1$ $\alpha=2.8$ $R_S=0.6$

EXAMPLE 5

Separation of enantiomers of timolol

Two chiral solid-phase chromatography materials were prepared according to the Examples above, with methacrylic acid and itaconic acid, respectively, as monomers. Both polymers with imprints of (S)(−)-timolol allowed base-line separation after application of a racemic mixture of timolol with $R_S$-values between 1.9 and 2.0 (see Table 1 and FIGS.

2A, B). The CSP obtained with methacrylic acid (MAA-CSP) also allowed separation of enantiomers of other β-blockers (see FIG. 1).

However, regarding the methacrylic acid polymer the resolution of racemic mixtures of metoprolol and atenolol was unsatisfactory (no data shown), but propranolol was resolved in a satisfactory manner ($K'_R$=1.0; δ=2.8; $R_S$=1.3). This agrees with previous results of enantiomer separation of amino acid derivatives of structurally related molecules with MAA-polymers (9). Owing to the high optical rotation values of propranolol, the enantiomer separation thereof could also be determined polarimetrically when the test concentration was increased to 20 g/l, In this manner it was determined that the peaks obtained by separation of the enantiomers were identical with those as measured by means of UV-absorption.

Regarding itaconic acid based polymers with molecular imprints (ITA-CSP), not only were sharper peaks obtained, but a higher degree of selectivity was also exhibited. By using (S)(–)-timolol as print molecule and subsequently applying an artificial mixture of the racemic aryloxipropanolamines timolol, propranolol, atenolol and metoprolol (structures, see FIG. 1), (S)(–)-timolol was retained in the most efficient manner of them all, while the others were neither separated in their enantiomer forms nor particularly bonded to the polymer (propranolol, $K'_{rac}$=0.2; atenolol and metoprolol, $K'_{rac}$=2.2; timolol, $K'_R$=2.5 and $K'_S$=3.6; flow rate 0.4 ml/min, UV-detection at 275 nm).

These results are probably caused by the fact that the neighbouring carboxyl groups on the bifunctional monomer itaconic acid which is used have a more pronounced possibility of interactions (reciprocal actions) with the heterocyclic side chain of timolol.

TABLE 1

Chromatographic resolution of timolol on chiral solid phases prepared by the molecular imprinting method by using (S)(-)-timolol as print molecule

| Functional monomer in the chiral solid phase | $k'_R$ | α | $R_S$ |
|---|---|---|---|
| Methacrylic acid (MMA) | 2.0 | 2.9 | 2.9 |
| Itaconic acid (ITA) | 1.4 | 2.5 | 1.9 |

FIG. 2 shows a diagram of the chromatographic resolution of timolol on polymers containing (A) methacrylic acid and (B) itaconic acid. The selected optimised eluants were acetonitrile/acetic acid (93/7, v/v) for (A) and ethanol/tetrahydrofuran/acetic acid (50/40/10, v/v/v) for (B). The test volume was 20 μl containing 20 μg β-blockers, the flow rate was 1 ml/min and the pressure about 30 bars. All separations were effected at ambient temperature and the UV-detection was made at 294 nm. The elution sequence was determined by injection of the pure enantiomers.

The capacity shown is perfectly well comparable with e.g. a biological alternative method using the protein cellulase (6d). The quantity of timolol with optimal baseline separation was 18.9 and 19.9 μg/g dry CSP, respectively, (FIG. 2) and in connection with the above-mentioned polarimetric study of propranolol with acceptable resolution but no base-line separation, 400 μg/g dry CSP.

Literature (1) (a) Richards, R.; Tattersfield, A. E., Br. J. Clin. Pharmacol. 1987, 24, 485–491. (b) Kloosterman, M.; Elferink, V. H. M.; van Iersel, J.; Meijer, E. M.; Hulshof, L. A.; Sheldon, R. A., Trends Biotechnol. 1988, 6, 251–256. (c) Walle, T.; Webb, J.; Bagwell, E.; Walle, K.; Daniell, H.; Gaffney, T., Biochem. Pharmacol. 1988, 37, 115–124. (d) Lindner, W.; Rath, M.; Stoschitzky, K.: Semmelrock, H. J., Chirality 1989, 1, 10–13.

(2) (a) Katsuki, T. Tetrahedron Lett. 1984, 25 (26), 2821–2822. (b) Klunder, J. M.; Ko, S. Y.; Sharpless, K. B., J. Org. Chem. 1986, 51, 3710–3712.

(3) (a) Matsuo, N.; Ohno, N., Tetrahedron Lett. 1985, 26 (45), 5533–5534. (b) Phillips, G. T.; Bertola, M. A.; Marx, A. F.; Koger, H. S., Eur. Pat. Appl. EP 256586, 1988, 9 pp.

(4) Oy Star AB, Neth. Appl. NL 8500939, 1988, 27 pp.

(5) (a) König, W. A.; Ernst, K., J. Chromatogr. 1983, 280, 135–141. (b) Isaksson, R.; Lamm, B. J., J. Chromatogr. 1986, 362, 436–438.

(6) (a) Armstrong, D. W.; Ward, T. J.; Armstrong, R. D.; Beesley, T. E., Science 1986, 232, 1132–1135. (b) Okamoto, Y.; Aburatami, R.; Hatano, K.; Hatada, K., J. Liq. Chromatogr. 1988, 11 (9–10), 2147–2163. (c) Aboul-Enein; Hassan, Y.; Islam, M. R., J. Chromatogr. 1990, 511, 109–114. (d) Erlandsson, P.; Marle, I.; Hansson, L.; Isaksson, R.; Pettersson, G.; Pettersson, C., J. Am. Chem. Soc. 1990, 112, 4573–4574.

(7) (a) Review: Wulff, G. In Polymeric Reagents and Catalysts; Ford, W. T., Ed.: ACS Symposium Series 208; American Chemical Society: Washington D.C., 1986; pp 186–230. (b) Sellergren, B.; Lepistö, M.; Mosbach, K., J. Am. Chem. Soc. 1988, 110, 5853–5860. (c) Shea, K. J.; Sasaki, D. Y., J. Am. Chem. Soc. 1989, 111, 3442–3444, (d) Ekberg, B.; Mosbach, K., Trends Biotechnol. 1989, 7, 92–96.

(8) Tate B., Adv. Polym. Sci. 1969, 5, 214–232.

(9) Andersson, L. I., Doctoral Thesis, University of Lund, Sweden, 1991.

We claim:

1. Method for separating enantiomers of a derivative of an aryloxipropanolamine comprising contacting the derivative with a chiral solid-phase chromatography material including molecular imprints of an optically pure enantiomer of the derivative to be separated.

2. The method as claimed in claim 1 wherein said chiral solid-phase chromatography material comprises a polymer which is prepared by polymerisation of a monomer in the presence of a cross-linking agent and a print molecule comprising the optically pure enantiomer of the derivative to be separated.

3. Chiral solid-phase chromatography material for use in the separation of enantiomers of derivatives of aryloxipropanolamine comprising:

a polymer prepared by polymerisation of a monomer in the presence of a cross-linking agent and an optically pure enentiomer of the derivative to be separated, a molecular imprint of the optically pure enantiomer being formed in the polymer by non-covalent interactions between the monomer and the optically pure enantiomer.

4. The chiral solid-phase chromatography material as claimed in claim 3 wherein the derivative of aryloxipropanolamine, which is used in the formation of the molecular imprint, is timolol, propranolol, metoprolol or atenolol.

5. The chiral solid-phase chromatography material as claimed in claim 3 wherein the monomer is a carboxyl-functional monomer.

6. The chiral solid-phase chromatography material as claimed in claim 5 wherein the carboxyl-functional monomer is itaconic acid.

7. The chiral solid-phase chromatography material as claimed in claim 5 wherein the carboxyl-functional monomer is methacrylic acid.

8. The chiral solid-phase chromatography material as claimed in claim 3, wherein the cross-linking agent is ethylene glycol dimethylacrylate.

9. Method for preparing a chiral solid-phase chromatography material for use in the separation of enantiomers of a derivative of an aryloxipropanolamine comprising polymerizing a monomer in the presence of a cross-linking agent and a print molecule comprising the optically pure enantiomer of the derivative to be separated.

10. The chiral solid-phase chromatography material as claimed in claim 4, wherein the monomer is a carboxyl-functional monomer.

11. The chiral solid-phase chromatography material as claimed in claim 4, wherein the cross-linking agent is ethylene glycol dimethylacrylate.

12. The chiral solid-phase chromatography material as claimed in claim 5, wherein the cross-linking agent is ethylene glycol dimethylacrylate.

13. The chiral solid-phase chromatography material as claimed in claim 6, wherein the cross-linking agent is ethylene glycol dimethylacrylate.

14. The chiral solid-phase chromatography material as claimed in claim 7, wherein the cross-linking agent is ethylene glycol dimethylacrylate.

* * * * *